United States Patent [19]

Takahashi et al.

[11] Patent Number: 5,079,000
[45] Date of Patent: Jan. 7, 1992

[54] CLATHRATE COMPOSITION INCLUDING ESSENTIAL OILS AND METHOD OF USING SAME

[75] Inventors: Ryoichi Takahashi; Tsuneo Mukai; Shigeyuki Mayama, all of Tokyo, Japan

[73] Assignee: Kurita Water Industries Ltd., Tokyo, Japan

[21] Appl. No.: 438,838

[22] Filed: Nov. 20, 1989

[30] Foreign Application Priority Data

Nov. 24, 1988 [JP] Japan .................. 63-297071

[51] Int. Cl.$^5$ .................. A61K 35/78; A61K 31/715; A61K 31/60; A61K 31/11
[52] U.S. Cl. .................. 424/195.1; 514/58; 514/159; 514/699; 514/731
[58] Field of Search .................. 514/58, 616, 159, 699, 514/731; 424/411, 195.1

[56] References Cited

U.S. PATENT DOCUMENTS

| | | | |
|---|---|---|---|
| 3,607,863 | 9/1971 | Dosch | 260/209 |
| 4,524,068 | 5/1985 | Szejtli | 514/58 |
| 4,636,343 | 1/1987 | Shibanai | 264/118 |
| 4,644,021 | 2/1987 | Toda | 523/122 |
| 4,728,510 | 3/1988 | Shibanai | 424/94.5 |
| 4,769,242 | 9/1988 | Shibanai | 424/411 |
| 4,780,317 | 10/1988 | Sekikawa | 424/468 |
| 4,818,771 | 4/1989 | Toda | 514/616 |
| 4,826,963 | 5/1989 | Stadler | 536/103 |
| 4,871,541 | 10/1989 | Shibanai | 424/411 |

FOREIGN PATENT DOCUMENTS 0329312  8/1989  European Pat. Off. .

*Primary Examiner*—Johnnie R. Brown
*Assistant Examiner*—Ralph Gitomer
*Attorney, Agent, or Firm*—Kanesaka and Takeuchi

[57] ABSTRACT

A composition for killing harmful organisms, which contains a clathrate compound composed of one or more natural essential oils and/or derivatives thereof selected from the group consisting of the following substances (1) to (22) and a polymolecular host compound capable of including the natural essential oils and/or derivatives thereof:

(1) hinoki oil;
(2) 1,8-cineole;
(3) l-α-terpineole;
l-carbone;
(5) l-menthone;
(6) d-pulegone;
(7) citronellal;
(8) linelool oxide;
(9) d,l-citronellol;
(10) 3,3,5-trimethylcyclohexanol;
(11) l-perillaldehyde;
(12) l-carveol;
(13) myrtenal;
(14) peppermint oil;
(15) eucalyptus oil;
(16) cinnamic aldehyde;
(17) α-bromo-cinnamic aldehyde;
(18) salicylaldehyde;
(19) benzaldehyde;
(20) paraphenyl-propionaldehyde;
(21) paratolualdehyde; and
(22) l-menthol.

5 Claims, No Drawings

CLATHRATE COMPOSITION INCLUDING ESSENTIAL OILS AND METHOD OF USING SAME

FIELD OF THE INVENTION AND RELATED ART STATEMENT

The present invention relates to an agent for killing harmful organisms. In particular, it relates to a natural essential oil clathrate compound containing agent for killing harmful organisms, which has an effect of killing harmful organisms such as insects, bacteria or fungi and which is highly safe to human bodies. The agent of the invention is advantageous as the slow-releasability of the active ingredient is sufficient, the durability of the killing effect is long and the agent itself can be handled with ease.

Among agents for killing harmful organisms, which are used for inhibiting growth of pathogenic fungi and bacteria for causing diseases in stored goods and for killing bacteria, fungi and harmful insects, preservatives which are used for preserving agricultural products are designated as additives to foods. Of chemical synthetic products, at present, orthophenylphenol, sodium orthophenylphenol, diphenyl, thiabendazole and parahydroxybenzoic acid esters are accepted as additives to foods in Japan.

Various insecticidal, fungicidal and bactericidal agents are widely used for agricultural use as well as in toiletry goods for household use.

On the other hand, many of insecticidal, bactericidal and fungicidal agents are in the form of a volatile liquid, and because of the volatility they are effective in the initial stage of the use thereof but the effect could not last for a long period of time as they vapourize rapidly. In addition, as being liquid, they could not be handled without extreme difficulty. Where they are desired to be used as a shaped product, they have to be inconveniently penetrated into paper, fibrous substances or oil-absorbing substances. Even when they are used as such a shaped product, long durability of the effect could not be attained and the effective life of the product is therefore extremely short.

Hitherto, as a means of slow releasing the volatile liquid chemical agent, formation of clathrate compounds with cyclodextrin as well as formation of inorganic or organic microcapsules has been proposed.

However, the conventional agents for killing harmful organisms which have heretofore been proposed could not be said sufficiently safe to human bodies. For instance, in the case of preservatives for agricultural products, there are inevitably various limitations for the concentration of the chemical agents, the way how to use the agents and the kind of the agricultural products to which the agents may be applied, for the purpose of ensuring the safety of the preservatives themselves to human bodies, and therefore the preservatives could not be employed without difficulty.

Almost none of the other agricultural chemicals (phytopathogenic fungicides, herbicides, etc.) are ensured to be satisfactorily safe to human bodies, so that the chemicals have to be employed only in a low concentration. Under the situation, a so-called chemical-free cultivation is being proposed and actually practised in some field.

For toiletry goods for household use, chemical agents which are more safe to human bodies are also desired.

On the other hand, there are various problems on the technique of slow-release of volatile liquid chemical agents. For instance, cyclodextrin-clathrate compounds have the following drawbacks. Specifically, cyclodextrin has a small space with a constant capacity for including a guest substance so that the guest substance which can be included in cyclodextrin is limiting. In addition, in the cyclodextrin clathrate compound, the guest substance is firmly and tightly included in the host cyclodextrin crystal so that it is hardly released under an ordinary condition. In order to release the guest substance from the clathrate compound, therefore, heat, pressure, enzyme or the like aid would have to be applied to the compound. However, application of such aid could not be said practical.

In the case of microcapsule clathrate compounds, the guest substance could be released therefrom only after the capsules are broken. Therefore, the compounds also require some external force such as heat, pressure or the like, so as to release the guest substance therefrom.

OBJECTS AND SUMMARY OF THE INVENTION

The object of the present invention is to overcome the above-mentioned problems in the prior art techniques and to provide an agent or compound for killing harmful organisms which has excellent insecticidal, bactericidal and fungicidal effects and which are satisfactorily safe to human bodies.

Another object of the present invention is to provide an agent for killing harmful organisms which has excellent slow-releasability of the active ingredient, excellent long durability of the effect and easy handling of the agent itself.

In order to attain the objects, there is provided in accordance with the present invention an agent for killing harmful organisms, which contains a clathrate compound composed of one or more natural essential oils and/or derivatives thereof as selected from the group consisting of the following substances (1) to (22) and a polymolecular host compound capable of including the said natural essential oils and/or derivatives thereof:

(1) hinoki oil;
(2) 1,8-cineole;
(3) l-α-terpineole;
(4) l-carbone;
(5) l-menthone;
(6) d-pulegone;
(7) citronellal;
(8) linalool oxide;
(9) d,l-citronellol;
(10) 3,3,5-trimethylcyclohexanol;
(11) l-perillaldehyde;
(12) l-carveol;
(13) myrtenal;
(14) peppermint oil;
(15) eucalyptus oil;
(16) cinnamic aldehyde;
(17) α-bromo-cinnamic aldehyde;
(18) salicylaldehyde;
(19) benzaldehyde;
(20) paraphenyl-propionaldehyde;
(21) paratolualdehyde; and
(22) l-menthol.

There is further provided in accordance with the present invention a method of preparing the agent for killing harmful organisms, in which one or more natural essential oils and/or derivatives thereof as selected from the group consisting of the above-mentioned substances (1) to (22) are brought into contact and reacted with a polymolecular host compound capable of including the said natural essential oils and/or derivatives thereof.

DETAILED DESCRIPTION OF PREFERRED EMBODIMENTS

Next, the present invention will be explained in detail hereunder.

The active ingredient of the harmful organisms-killing agent of the present invention comprises one or more natural essential oils and/or derivatives thereof of the above-mentioned substances (1) to (22).

The harmful organisms-killing agent of the present invention contains a clathrate compound composed of the active ingredient of the above-mentioned natural essential oil(s) and/or derivative(s) thereof, as a guest compound, and a polymolecular host compound capable of including the guest compound.

As examples of the polymolecular host compounds capable of including the natural essential oil(s) and/or derivative(s) thereof of the above-mentioned substances (1) to (22), which are employable in the present invention, there are mentioned various polymolecular host compounds such as acetylene alcohol compounds, phenol compounds, diol compounds, amide compounds, cyclooctane compounds, cholic acid compounds, etc. Specifically, one or more compounds selected from the group consisting of the following compounds (1) to (22) can be employed.

(1) 1,1,6,6-Tetraphenyl-2,4-hexadiyne-1,6-diol
(2) 1,6-Bis(2-chlorophenyl)-1,6-diphenylhexa-2,4-diyne-1,6-diol
(3) 1,1-Di(2,4-dimethylphenyl)-2-propyn-1-ol
(4) 2,5-Di(2,4-dimethylphenyl)hydroquinone
(5) 1,1,4,4-Tetraphenyl-2-butyne-1,4-diol
(6) 1,1,2,2-Tetraphenylethane-1,2-diol
(7) 1,1-Bi-2-naphthol
(8) 9,10-Diphenyl-9,10-dihydroanthracene-9,10-diol
(9) 1,1,6,6-Tetra(2,4-dimethylphenyl)-2,4-hexadiyne-1,6-diol
(10) 9,10-Di(4-methylphenyl)-9,10-dihydroanthracene-9,10-diol
(11) 1,1-Bis(4-hydroxyphenyl)cyclohexane
(12) Diphenic acid bis(dicyclohexylamide)
(13) 1,4-Diaza-bi(cyclo-2,2,2-octane)
(14) Bis(4-hydroxyphenyl)sulfone
(15) 4,4'-Butylidene-bis(3-methyl-6-t-butylphenol)
(16) 2,2'-Methylene-bis(4-methyl-6-t-butylphenol)
(17) 4,4'-Thio-bis(3-methyl-6-t-butylphenol)
(18) 2,2'-Methylenbis(4-chlorophenol)
(19) Deoxycholic acid
(20) T-butylhydroquinone
(21) 2,5-Di-t-butylhydroquinone
(22) Cholic acid The clathrate compound composed of the polymolecular host compound and the guest compound of natural essential oil(s) and /or derivative(s) thereof of the above-mentioned substances (1) to (22) can be prepared with ease by the method of the present invention, where a determined amount of the host compound and a determined amount of the guest compound are blended and stirred for direct contact reaction therebetween to give the intended clathrate compound or, alternatively, the host compound and the guest compound are stirred and reacted in an organic solvent to give the intended clathrate compound. In the latter case of using an organic solvent, preferred examples of usable organic solvents are methanol, ethanol, n-propanol, acetone, benzene, chlorofrom, ethyl acetate, dipropyl ether, etc.

The reaction time may be generally approximately 5 minutes or so. The reaction may be effected at room temperature. After the reaction mixture is solidified, the reaction is stopped. The intended clathrate compound is formed, in general, as a solid, and the formation of the compound can be confirmed with ease by IR spectrography.

In the harmful organisms-killing agent of the present invention, the included proportion of the guest compound of the active ingredient is preferably larger in view of the harmful organisms-killing effect of the agent. In general, however, the proportion of the guest compound to the polymolecular host compound in the clathrate compound of the invention may fall within the range of from 10/90 to 70/30 by weight. Accordingly, in the method of producing the clathrate compound of the present invention, the amount of the host compound and the amount of the guest compound to be reacted are properly determined so that the proportion of the two compound in the clathrate compound to be formed may fall within the range.

As a means of practically using the harmful organisms-killing agent of the present invention, which contains the above-mentioned clathrate compound, for example, the following methods (a) to (e) are mentioned.

(a) The clathrate compound is powdered or granulated and the resulting powder or granules are directly sprayed over the object to be treated.

(b) The clathrate compound is powdered or granulated, the resulting powder or granules are dispersed in water or a pertinent medium, and the resulting dispersion is sprayed over the object to be treated.

(c) The clathrate compound is shaped into tablets, spherical beads or the like, which are put on the place to be treated. In this case, calcium silicate, magnesium silicate, titanium oxide, crystalline cellulose or the like can be used as a shaping aid.

(d) The shaped products prepared in (c) are combined in a ventilating device and a gaseous stream containing the active ingredient is blown into the place to be treated therefrom.

(e) The clathrate compound is wrapped with a gas-permeable sheet substance such as paper or the like and is used as a sheet product.

However, the means of using the harmful organisms-killing agent of the present invention is not whatsoever limited to only the above-mentioned methods (a) to (e), but the agent may also be used as a coating composition or adhesive or may also be incorporated into any other plastic resins.

Therefore, in accordance with the above-mentioned application embodiments, the harmful organisms-killing agent of the present invention can be applied to various uses in various domestic, agricultural and industrial fields, for example as a solid slow-release agent for killing harmful organisms, a harmful organisms-killing paper having an excellent long effect life, a harmful organisms-killing plastic sheet, a harmful organisms-killing plate, a harmful organisms-killing coating composition, a harmful organisms-killing adhesive, a harmful organisms-killing spray, a harmful organisms-killing cream, etc.

In particular, the harmful organisms-killing agent of the present invention is effectively usable for inhibiting growth of various pathogenic fungi and bacteria of causing diseases in stored goods as well as for killing harmful insects.

As the pathogenic fungi and bacteria of causing diseases in stored goods, to which the harmful organisms-killing agent of the present invention is advantageously applicable, there are mentioned, for example, anthracnose (Colletotrichum), gray fungi (Botrytis), white fungi (Geotricum, Candida), green fungi (Penicillium), Fusarium, black spot fungi (Alternaria), etc. However, these are not limitative.

As examples of fruits and vegetables which are protected from the pathogenic fungi and bacteria by the use of the agent of the present invention, there are mentioned mandarine oranges, piments, grapes, carrots, strawberries, pumpkins, oranges, lemons, grapefruits, watermelons, apples, etc. Needless to say, the agent of the present invention is of course effective to any other fruits and vegetables.

As the harmful insects and acarids to which the agent of the present invention is effectively applied for killing them, there are mentioned leaf acarids, aphides, etc. As examples of fruits and vegetables which are protected from the harmful insects and acarids by the use of the agent of the present invention, there are mentioned tomatoes and cucumbers in addition to the fruits and vegetables mentioned above. However, these are not also limitative.

In the harmful organisms-killing agent of the present invention, the natural essential oils and/or derivatives thereof of the above-mentioned substances (1) to (22) which are used as the active ingredient in the clathrate compounds have an extremely excellent effect of inhibiting growth of pathogenic fungi and bacteria of causing diseases in stored goods and also an extremely effect of killing harmful insects, while they are highly satisfactorily safe to human bodies as they are natural essential oils and derivatives thereof which are accepted as food additives.

Accordingly, the use of the harmful organisms-killing agent of the present invention is almost unlimitative and therefore can effectively be utilized for various industrial and domestic uses in a broad range.

On the other hand, the polymolecular host compounds for use in the present invention have a sufficiently high capacity of including the natural essential oils and/or derivatives thereof of the above-mentioned substances (1) to (22) and therefore they may extremely safely include them as a guest compound to give the intended clathrate compound. In addition, the thus formed clathrate compound may pertinently slowly release the guest compound therefrom.

Accordingly, the clathrate compound of the present invention may stably include and protect the active ingredient of the said natural essential oil(s) and/or derivative(s thereof so as to inhibit the vaporization of the active ingredient, while the resulting clathrate compound may properly slowly release the active ingredient therefrom after applied to the object to be protected from harmful organisms.

Therefore, the clathrate compound of the present invention may stably have the excellent harmful organisms-killing effect of the active ingredient for a long period of time. Moreover, as the clathrate compound of the present invention is provided in the form of a solid, the handlability and shapability of the compound are good. Therefore, the harmful organisms-killing agent of the present invention can be utilized for various uses in various fields.

Next, the present invention will be explained in more detail by way of the following examples and comparative examples, but the present invention is not limited to only the following examples without departing from the spirit and scope thereof.

EXAMPLE 1

Insecticidal Test with Hinoki Oil-Clathrate Compound

Hinoki oil and 1,1-bis-(4-hydroxyphenyl)cyclohexane were reacted for 10 minutes at room temperature by direct contact reaction to obtain a hinoki oil-clathrate compound having a hinoki oil-included proportion of 30 % by weight.

The clathrate compound was dispersed in water to prepare a suspension having a determined concentration, whereupon a surfactant was used as a dispersion stabilizer. The suspension thus prepared was sprayed over leaves of tomato plants as damaged by aphides with a spray, the amount of the suspension sprayed being shown in Table 1 below. Afterwards, the thus sprayed leaves were allowed to stand in an open-air condition at room temperature. After 24 hours and 48 hours, the proportion of the died aphides was measured, and the results obtained are shown in Table 1.

The judgement of living aphides or died aphides was conducted by applying stimulation with a needle to all the aphides on the leaves under observation with a microscope.

COMPARATIVE EXAMPLE 1

Other suspensions were prepared in the same manner as in Example 1, except that hinoki oil was used in place of the hinoki oil clathrate compound, and these were subjected to the same insecticidal test. The results are also shown in Table 1.

COMPARATIVE EXAMPLE 2

The same insecticidal test as in Example 1 was carried out, except that no chemical was sprayed to the tomato leaves. The results are shown in Table 1.

TABLE 1

| Example | No. | Chemical Agent Applied | Pure Content of Hinoki Oil Sprayed (g/m$^2$) | Proportion of Died Aphides (%) | |
|---|---|---|---|---|---|
| | | | | After 24 hours | After 48 hours |
| Example 1. | 1 | Hinoki Oil Clathrate Compound | 0.03 | 30 | 41 |
| | 2 | " | 0.15 | 33 | 58 |
| | 3 | " | 0.3 | 44 | 91 |
| | 4 | " | 1.5 | 91 | 100 |
| | 5 | " | 3.0 | 100 | 100 |
| Comparative | 6 | Hinoki Oil | 0.03 | 0 | 0 |
| Example 1 | 7 | " | 0.15 | 5 | 10 |
| | 8 | " | 0.3 | 8 | 15 |
| | 9 | " | 1.5 | 19 | 22 |

TABLE 1-continued

| Example | No. | Chemical Agent Applied | Pure Content of Hinoki Oil Sprayed (g/m$^2$) | Proportion of Died Aphides (%) | |
|---|---|---|---|---|---|
| | | | | After 24 hours | After 48 hours |
| | 10 | " | 3.0 | 32 | 35 |
| Comparative Example 2 | 11 | No Sprayed | 0 | 0 | 0 |

As is obvious from the results in Table 1 above, the hinoki oil-clathrate compound has a longer effect-durability than the hinoki oil itself as the former releases the hinoki oil component slowly. Therefore, the aphides-killing effect of the hinoki oil-clathrate compound is higher than that of the hinoki oil itself.

EXAMPLE 2

Test for Inhibiting Growth of Gray Fungi

Using the chemical substances shown in Table 2 as the guest compound and 1,1-bis-(4-hydroxyphenyl)cyclohexane as the host compound (provided that 2,5-di-t-butylhydroquinone was used to the guest compound 1,8-cineole), clathrate compounds were prepared, whereupon the included proportion of the guest compound was 27 % by weight in every case. The reaction temperature was room temperature and the reaction time was 10 minutes. The guest compound and the host compounds were reacted by direct contact reaction.

On the other hand, gray fungi were inoculated in the center of a 9 cm-laboratory dish having a PDA (potato-dextrose-agar) dish therein, and the dish was put in a 10 liter-plastic container. 1 g of the clathrate compound prepared above was uniformly applied to the periphery of the dish (which corresponded to 27 mg/liter of the active ingredient), and the fungi were incubated at room temperature while the plastic container was opened. After incubated for 7 days, the diameter (cm) of the colony was observed, and the results obtained are shown in Table 2.

COMPARATIVE EXAMPLE 3

The same test as in Example 2 was carried out, except that no chemical substance was applied to the test dish. The results obtained are also shown in Table 2.

TABLE 2

| | | | (Diameter of Colony: cm) | |
|---|---|---|---|---|
| | | Chemical Substance | Gray Fungi | |
| Example | No. | (Active Substance Included) | Strawberry | Pumpkin |
| Example 2 | 12 | Hinoki Oil | 4.0 | 1.2 |
| | 13 | 1,8-Cineole | 2.3 | 1.0 |
| | 14 | l-α-terpineole | 5.0 | 2.0 |
| | 15 | l-Carbone | 3.7 | 1.5 |
| | 16 | l-menthone | 3.0 | 2.2 |
| | 17 | d-Pulegone | 2.7 | 1.7 |
| | 18 | Citronellal | 1.5 | 1.0 |
| | 19 | Linalool Oxide | 5.5 | 2.4 |
| | 20 | d,l-citronellol | 5.4 | 2.5 |
| | 21 | 3,3,5-Trimethylcyclohexanol | 1.4 | 1.2 |
| | 22 | l-perillaldehyde | 1.7 | 0.3 |
| | 23 | l-carveol | 5.5 | 1.7 |
| | 24 | Myrtenal | 2.8 | 0.8 |
| | 25 | Peppermint Oil | 3.5 | 2.1 |
| | 26 | Eucalyptus Oil | 3.2 | 1.9 |
| Comparative Example 3 | 27 | Not Added | more than 9 | more than 9 |

EXAMPLE 3

Test for Inhibiting Growth of Anthracnose Fungi (Colletotrichum citri):

The same l-carbone, 3,3,5-trimethylcyclohexanol or myrtenal clathrate compound as that used in Example 2 was subjected to a test for inhibiting growth of anthracnose fungi (Colletotrichum citri) in the same procedure for the test of Example 2. The results obtained are shown in Table 3 below.

COMPARATIVE EXAMPLE 4

The same test as in Example 3 was carried out, except that 0.27 g of a simple substance of the guest compound was used in place of the clathrate compound. The results obtained are also shown in Table 3.

COMPARATIVE EXAMPLE 5

The same test as in Example 3 was carried out, except that no chemical substance was employed. The results obtained are shown in Table 3.

TABLE 3

| | | (Diameter of Colony: cm) | |
|---|---|---|---|
| Example | No. | Chemical Substance | Anthracnose Fungi (Colletotrichum citri) |
| Example 3 | 28 | l-carbone Clathrate Compound | 5.9 |
| | 29 | 3,3,5-Trimethylcyclohexanol Clathrate Compound | 2.3 |
| | 30 | Myrtenal Clathrate Compound | 4.1 |
| Comparative Example 4 | 31 | l-carbone | 7.7 |
| | 32 | 3,3,5-Trimethylcyclohexanol | 7.8 |
| | 33 | Myrtenal | 7.9 |

TABLE 3-continued

| | | | (Diameter of Colony: cm) |
|---|---|---|---|
| Example | No. | Chemical Substance | Anthracnose Fungi (*Colletotrichum citri*) |
| Comparative Example 5 | 35 | Not Added | more than 9 |

EXAMPLE 4

Test for Inhibiting Growth of White Fungi

The same citronellal or l-perillaldehyde clathrate compound as that used in Example 2 was subjected to a test for inhibiting growth of white fungi. As the white fungi to be tested, those derived from orange, lemon, mandarine orange and grapefruit were used, and the test was carried out in the same procedure as that in Example 2. The results obtained are shown in Table 4 below.

COMPARATIVE EXAMPLE 6

The same test as in Example 4 was carried out, except that 0.27 g of a simple substance of the guest compound was used in place of the clathrate compound. The results obtained are also shown in Table 4.

COMPARATIVE EXAMPLE 7

The same test as in Example 4 was carried out, except that no chemical substance was employed. The results obtained are shown in Table 4.

EXAMPLE 5

Test for Inhibiting Growth of Fusarium Fungi, Black Spot Fungi and Green Fungi

Using the chemical agents as shown in Table 5 below, the fungi growth-inhibiting test was carried out in the same procedure as in Example 2. The results obtained are shown in Table 5.

COMPARATIVE EXAMPLE 8

The same test as in Example 5 was carried out, except that 0.27 g of a simple substance of the guest compound was used in place of the clathrate compound. The results obtained are also shown in Table 5.

COMPARATIVE EXAMPLE 9

The same test as in Example 5 was carried out, except that no chemical substance was employed. The results obtained are shown in Table 5.

TABLE 5

| | | | (Diameter of Colony: cm) | | |
|---|---|---|---|---|---|
| Example | No. | Chemical Substance | *Fusarium oxysporum* | *Alternaria citri* | *Penicillium citri* |
| Example 5 | 40 | Hinoki Oil Clathrate Compound | 8.0 | 5.2 | 3.5 |
| | 41 | 1,8-Cineole Clathrate Compound | 4.7 | 5.1 | 3.0 |
| | 42 | 3,3,5-Trimethylcyclohexanol Clathrate Compound | 2.8 | 3.3 | 2.2 |
| | 43 | l-perillaldehyde Clathrate Compound | 5.6 | 5.5 | 1.7 |
| | 44 | Myrtenal Clathrate Compound | 3.5 | 1.9 | 0.9 |
| | 45 | Citronellal Clathrate Compound | 2.7 | 3.3 | 2.2 |
| Comparative Example | 46 | Hinoki Oil | more than 9 | 5.6 | 7.0 |
| | 47 | 1,8-Cineole | more than 9 | 7.0 | 7.0 |
| | 48 | 3,3,5-Trimethylcyclohexanol | 8.2 | 7.4 | more than 9 |
| | 49 | l-perrilaldehyde | more than 9 | 7.7 | 6.8 |
| | 50 | Myrtenal | more than 9 | 6.4 | 5.3 |
| | 51 | Citronellal | more than 9 | 7.1 | 7.0 |
| Comparative Example 9 | 52 | Not Added | more than 9 | 7.8 - | 7.0 |

From the results in Table 2 to Table 5, it is obvious that the clathrate compounds of the present invention were effective for a long period of time since they gradually and slowly released the active ingredient therefrom, and accordingly, the fungi growth-inhibiting effect of the clathrate compound was higher than that of the corresponding simple substance of the active ingredient.

TABLE 4

| | | | (Diameter of Colony: cm) | | | |
|---|---|---|---|---|---|---|
| | | | White Fungi | | | |
| Example | No. | Chemical Substance | Orange | Lemon | Mandarine Orange | Grapefruit |
| Example 4 | 35 | Citronellal Clathrate Compound | 2.0 | 2.2 | 2.3 | 1.8 |
| | 36 | l-perillaldehyde Clathrate Compound | 3.5 | 5.5 | — | 6.5 |
| Comparative Example 6 | 37 | Citronellal | 7.5 | 8.4 | 7.2 | 6.3 |
| | 38 | l-perillaldehyde | 8.2 | 8.7 | — | — |
| Comparative Example 7 | 39 | Not Added | more than 9 | more than 9 | more than 9 | more than 9 |

While the invention has been described in detail and with reference to specific embodiments thereof, it will be apparent to one skilled in the art that various changes and modifications can be made therein without departing from the spirit and scope thereof.

What is claimed is:

1. A composition for killing harmful fungi, bacteria and insects, comprising a clathrate compound composed of at least one natural essential oil selected from the group consisting of the following substances (1) to (22) and a host compound capable of including said natural essential oils, said host compound being selected from the group consisting of acetylene alcohols, phenols, amides and cyclooctanes, proportion of the natural essential oil to the host compound being in the range from 10/90 to 70/30 by weight:
   (1) hinoki oil;
   (2) 1,8-cineole;
   (3) l-α-terpineole;
   (4) l-carbone;
   (5) l-methone;
   (6) d-pulegone;
   (7) citronellal;
   (8) linalool oxide;
   (9) d,l-citronellol;
   (10) 3,3,5-trimethylcyclohexanol;
   (11) l-perillaldehyde;
   (12) l-carveol;
   (13) myrtenal;
   (14) peppermint oil;
   (15) eucalyptus oil;
   (16) cinnamic aldehyde;
   (17) α-bromo-cinnamic aldehyde;
   (18) salicylaldehyde;
   (19) benzaldehyde;
   (20) paraphenyl-propionaldehyde;
   (21) paratolualdehyde; and
   (22) l-menthol.

2. A composition for killing harmful fungi, bacteria and insects as claimed in claim 1, in which the host compound is at least one compound selected from the group consisting of the following substances:
   1,1-Di(2,4-dimethylphenyl)-2-propyn-1-ol
   2,5-Di(2,4-dimethylphenyl)hydroquinone
   1,1-Bi-2-naphthol
   1,1-Bis(4-hydroxyphenyl)cyclohexane
   Diphenic acid bis(dicyclohexylamide)
   1,4-Diaza-bi(cyclo-2,2,2-octane)
   Bis(4-hydroxyphenyl)sulfone
   4,4'-Butylidene-bis(3-methyl-6-t-butylphenol)
   2,2'-Methylene-bis(4-methyl-6-t-butylphenol)
   4,4'-Thio-bis(3-methyl-6-t-butylphenol)
   2,2'-Methylenbis(4-chlorophenol)
   T-butylhydroquinone
   2,5-Di-t-butylhydroquinone.

3. A method of preventing growth of harmful fungi, bacteria and insects, comprising applying to the harmful fungi, bacteria and insects with a material containing a clathrate compound composed of at least one natural essential oil selected from the group consisting of the following substances (1) to (22) and a host compound capable of containing said natural essential oils, said host compound being selected from the group consisting of acetylene alcohols, phenols, amides and cyclooctanes, proportion of the natural essential oil to the host compound being in the range from 10/90 to 70/30 by weight:
   (1) hinoki oil;
   (2) 1,8-cineole;
   (3) l-α-terpineole;
   (4) l-carbone;
   (5) l-menthone;
   (6) d-pulegone;
   (7) citronellal;
   (8) linalool oxide;
   (9) d,l-citronellol;
   (10) 3,3,5-trimethylcyclohexanol;
   (11) l-perillaldehyde;
   (12) l-carveol;
   (13) myrtenal;
   (14) peppermint oil;
   (15) eucalyptus oil;
   (16) cinnamic aldehyde;
   (17) α-bromo-cinnamic aldehyde;
   (18) salicylaldehyde;
   (19) benzaldehyde;
   (20) paraphenyl-propionaldehyde;
   (21) paratolualdehyde; and
   (22) l-menthol.

4. A method as claimed in claim 3, in which the host compound is at least one compound selected from the group consisting of the following substances:
   1,1-Di(2,4-dimethylphenyl)-2-propyn-1-ol
   2,5-Di(2,4-dimethylphenyl)hydroquinone
   1,1-Bi-2-naphthol
   1,1-Bis(4-hydroxyphenyl)cyclohexane
   Diphenic acid bis(dicyclohexylamide)
   1,4-Diaza-bi(cyclo-2,2,2-octane)
   Bis(4-hydroxyphenyl)sulfone
   4,4'-Butylidene-bis(3-methyl-6-t-butylphenol)
   2,2'-Methylene-bis(4-methyl-6-t-butylphenol)
   4,4'-Thio-bis(3-methyl-6-t-butylphenol)
   2,2'-Methylenbis(4-chlorophenol)
   T-butylhydroquinone
   2,5-Di-t-butylhydroquinone.

5. A method as claimed in claim 3, wherein the natural essential oil is applied to harmful fungi and bacteria in stored agricultural products.

* * * * *